(12) United States Patent
Sun et al.

(10) Patent No.: US 11,638,934 B2
(45) Date of Patent: May 2, 2023

(54) OPTICAL WINDOW CLEANING DEVICE, OPTICAL WINDOW CLEANING METHOD AND UNDERWATER OPTICAL DEVICE (71) Applicant: PENG CHENG LABORATORY, Shenzhen (CN)

(72) Inventors: Caiming Sun, Shenzhen (CN); Aidong Zhang, Shenzhen (CN); Jing Lin, Shenzhen (CN); Xinke Tang, Shenzhen (CN)

(73) Assignee: PENG CHENG LABORATORY, Shenzhen (CN)

( * ) Notice: Subject to any disclaimer, the term of this patent is extended or adjusted under 35 U.S.C. 154(b) by 0 days.

(21) Appl. No.: 17/887,128

(22) Filed: Aug. 12, 2022

(65) Prior Publication Data
US 2022/0379350 A1 Dec. 1, 2022

Related U.S. Application Data (63) Continuation of application No. PCT/CN2021/071346, filed on Jan. 13, 2021.

(30) Foreign Application Priority Data

Feb. 13, 2020 (CN) .......................... 202010091069.5

(51) Int. Cl.
B08B 1/04 (2006.01)
B08B 1/00 (2006.01)
B08B 3/02 (2006.01)

(52) U.S. Cl.
CPC ................ B08B 1/04 (2013.01); B08B 1/002 (2013.01); B08B 3/024 (2013.01)

(58) Field of Classification Search
CPC .......... B08B 1/04; B08B 1/002; B08B 3/024; B08B 1/00; B08B 3/02; B08B 1/005;
(Continued)

(56) References Cited

U.S. PATENT DOCUMENTS 3,832,750 A * 9/1974 Jarvinen ................... B60S 1/60
15/250.16
8,567,963 B1 * 10/2013 Criscuolo .......... G02B 27/0006
359/507
(Continued)

FOREIGN PATENT DOCUMENTS

CN 2079482 U 6/1991
CN 1336881 A 2/2002
(Continued)

OTHER PUBLICATIONS

First Office Action issued in counterpart Chinese Patent Application No. 202010091069.5, dated Jan. 19, 2022.
(Continued)

Primary Examiner — Alexander Markoff
(74) Attorney, Agent, or Firm — Westbridge IP LLC (57) ABSTRACT Disclosed is an optical window cleaning device, including: a cleaning brush; and a wiper arm. The wiper arm includes a first link, a torsion mechanism, a second link and a wiper arm drive system. A second end of the first link is hinged to a first end of the second link. The cleaning brush is hinged to a first end of the first link, a rotation trajectory of the cleaning brush and a rotation trajectory of a hinge joint between the second end of the first link and the first end of the second link are both located in a first plane. A rotation trajectory of the second link and the rotation trajectory of the hinge joint are located in the first plane. The torsion mechanism provides the first link and the second link with a force that rotates the first link relative to the second link.

16 Claims, 7 Drawing Sheets (58) Field of Classification Search
CPC ...... B08B 2203/0217; A61L 2/10; A61L 2/18; A61L 2202/17
See application file for complete search history.

(56) References Cited

U.S. PATENT DOCUMENTS

| | | | | |
|---|---|---|---|---|
| 9,731,688 | B2* | 8/2017 | Doorley | B60S 1/44 |
| 9,855,925 | B2* | 1/2018 | Doorley | B60S 1/482 |
| 10,183,653 | B2* | 1/2019 | Davies | G02B 27/0006 |
| 10,782,520 | B2* | 9/2020 | Crespo | H04N 5/2252 |
| 11,097,695 | B2* | 8/2021 | Richardson | G02B 27/0006 |
| 11,279,324 | B2* | 3/2022 | Gilbertson | B60S 1/38 |
| 2002/0073493 | A1* | 6/2002 | Walton | E04H 4/1618 15/1.7 |
| 2008/0072393 | A1* | 3/2008 | Tanaka | A47L 1/02 15/250.03 |
| 2012/0167327 | A1* | 7/2012 | Kasack | F16L 29/007 15/250.04 |
| 2013/0104933 | A1* | 5/2013 | Aldred | G03B 17/561 134/6 |
| 2014/0196745 | A1* | 7/2014 | Whelan | B08B 17/02 134/1 |
| 2016/0121855 | A1* | 5/2016 | Doorley | B60S 1/566 15/250.01 |
| 2016/0238838 | A1 | 8/2016 | Tago | |
| 2017/0113658 | A1* | 4/2017 | Shimoyama | B60S 1/522 |
| 2017/0151933 | A1* | 6/2017 | Doorley | B60S 1/56 |
| 2020/0094786 | A1* | 3/2020 | Gilbertson | B60S 1/34 |
| 2022/0379350 | A1* | 12/2022 | Sun | B08B 3/02 |

FOREIGN PATENT DOCUMENTS

| | | | |
|---|---|---|---|
| CN | 102179389 | A | 9/2011 |
| CN | 104841655 | A | 8/2015 |
| CN | 105170508 | A | 12/2015 |
| CN | 205008291 | U | 2/2016 |
| CN | 205056525 | U * | 3/2016 |
| CN | 107139887 | A | 9/2017 |
| CN | 107377430 | A | 11/2017 |
| CN | 207491081 | U | 6/2018 |
| CN | 108769490 | A | 11/2018 |
| CN | 109454039 | A | 3/2019 |
| JP | H10216049 | A | 8/1998 |

OTHER PUBLICATIONS

International Search Report issued in corresponding PCT Application No. PCT/CN2021/071346, dated Apr. 1, 2021.
Written Opinion issued in corresponding PCT Application No. PCT/CN2021/071346, dated Apr. 1, 2021.

* cited by examiner

OPTICAL WINDOW CLEANING DEVICE, OPTICAL WINDOW CLEANING METHOD AND UNDERWATER OPTICAL DEVICE

CROSS-REFERENCE TO RELATED APPLICATIONS

This application is a continuation application of International Application No. PCT/CN2021/071346, filed on Jan. 13, 2021, which claims priority to Chinese Patent Application No. 202010091069.5, filed on Feb. 13, 2020. The disclosures of the above-mentioned applications are incorporated herein by reference in their entireties.

TECHNICAL FIELD

The present disclosure relates to the technical field of underwater optical devices, and in particular, to an optical window cleaning device, an optical window cleaning method and an underwater optical device.

BACKGROUND

More than 70% of the earth's surface is covered with water, and underwater environmental exploration, especially the ocean exploration, has gained a growing interest in recent years. Underwater networks with distributed nodes, such as Boats, Buoys, ROVs, AUVs and seabed nodes, are deployed to the underwater environment for collaborative sensing and monitoring. Underwater wireless communication (UWC) between the mobile or fixed underwater nodes therefore becomes an indispensable technology. UWC can be implemented through the use of radio frequency (RF) electromagnetic waves, acoustic waves and light waves. However, the radio frequency is greatly attenuated in the water, and the transmission distance is therefore very limited, while underwater acoustic communication suffers from limited bandwidth and relatively high latency, which is not suitable for high-speed underwater data transmission. Underwater wireless optical communication (UWOC) is an attractive alternative, in which the information is carried by the wirelessly transmitting light (i.e., optical signals). The UWOC has been shown as a promising approach with many advantages, such as wide bandwidth, high data transmission rate, low latency, small size, etc. Consequently, UWOC systems have been being developed and improved, such as described in US Patent Publication No. 795,332,6B2. UWOC devices and products are also commercialized in the recent years.

A UOWC device includes either a transmitter, a receiver, or both, enclosed within a water-proof container with an optical window. The devices are then installed on the aforementioned underwater network nodes and set up the wireless communication links. The transmitter may have one or more light sources (Light-Emitting Diodes or lasers) and electronics for driving, modulating and controlling the light sources. On the other hand, the receiver may include a photodiode or a photodiode array and corresponding amplification and processing circuits. The underwater data exchange is conducted by transferring the information in the form of light in two directions in the aqueous medium, from each optical transmitter to the corresponding optical receiver.

The transmitter and receiver at each party/node can be enclosed in separate housings, or in a single housing. Either way, the housing of such UWOC devices practically features a water-proof container with an optical window.

Figure 1:
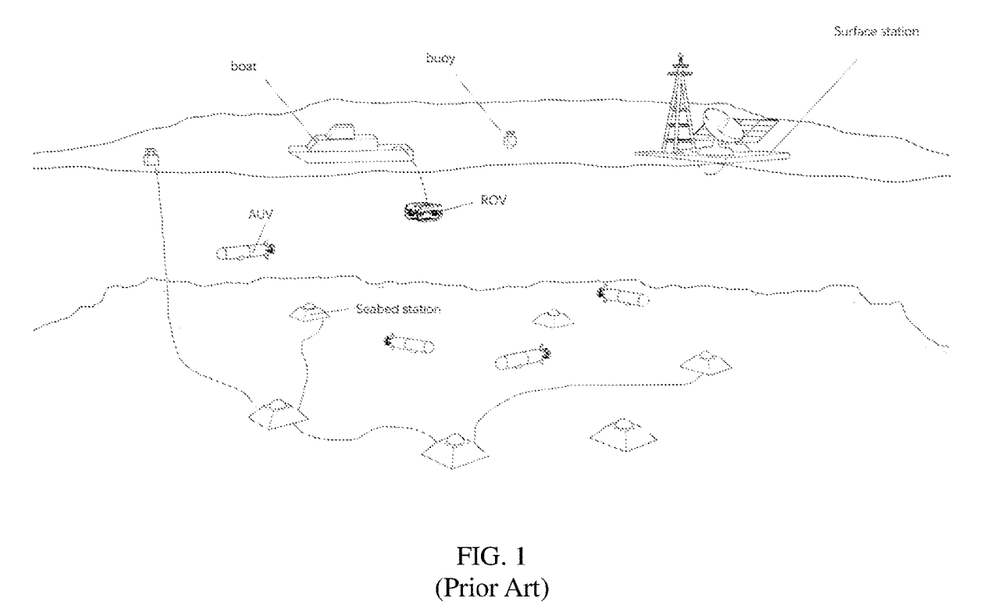
FIG. 1 a schematic diagram of an underwater network based on the UWOC technology in the prior art.

FIG. 1 is a schematic diagram of an underwater network based on the UWOC technology. There are surface nodes: boats, buoys, surface stations, underwater vehicles: ROVs, AUVs and a group of seabed nodes. These nodes are equipped with UWOC devices to accomplish the communication task between them and hence collaboratively conduct underwater environment exploration. In usage scenarios, the buoy on the water surface can be wired to the seabed nodes, which are then wirelessly connected with other nodes. Besides, the buoy can be also a wireless node with an UWOC device, which is sending/receiving data from AUVs, ROVs, seabed nodes. The UWOC device carried by each wireless node will have optical windows covering its output/input ports.

As the communication relies on the propagation of optical signals from a light emitting element (i.e., Light-Emitting Diode or laser) to a photodetector, the optical windows of UWOC devices must be optically transparent and any form of shading will affect the quality of data transmission. However, when the UWOC device works underwater, sea animals and plants will stick to the optical windows, affecting the signal transmission. To ensure that the UWOC device works effectively, it is necessary to try to remove the attached organisms on the optical windows.

In order to solve the problem of sea organisms adhering to the optical windows of UWOC device when it works underwater, many anti-biofouling approaches have been proposed in recent years, which are mainly divided into the following categories. 1. Anti-biofouling coatings/paints are used, but this method cannot be applied to the above communication devices since the coatings reduce the transparency and increase the roughness which affects the transmission and refraction of optical signals. 2. UV radiation can be also used to prevent biofouling on the surface. However, the efficiency of this method highly depends on the exposure time and energy of the surface. Therefore, solely applying UV radiation to prevent the bio-fouling will dramatically increase the system power consumption and is not suitable for unwired, self-contained devices such as AUVs and standalone seabed nodes. 3. A mechanical device is used to mechanically scrape off attached organisms. Compared with the method relying solely on ultraviolet radiation, it consumes less energy, and removes attached organisms without affecting the normal operation of optical communication equipments. To sum up, the method of scraping off the sea creatures attached to the optical window surface with a mechanical device is more suitable for the characteristics of UWOC device and its application scenarios.

Practically, the optical windows of UWOC devices are normally deigned as hemispherical or other curved shapes rather than flat plates, in order to match the transmitter/receiver's active area, meet the desired light direction and field, as well as against underwater pressure. Therefore, it is desirable to develop an effective anti-biofouling method for UWOC device that can be applied to the optical window of arbitrary geometry (e.g., a spherical surface with different curvature radius, a multi-faceted sphere or a polyhedron), and at the same time, to ensure the long-term use effect, it is necessary to have the function of cleaning the cleaning blade.

SUMMARY

In view of this, the present disclosure provides an optical window cleaning device, which is suitable for cleaning surfaces of polyhedral windows and spherical windows with varying curvatures.

The present disclosure also provides an optical window cleaning method and an underwater optical device using the above device.

In order to achieve the above objective, the present disclosure provides an optical window cleaning device, including a cleaning brush and a wiper arm. The wiper arm includes a first link, a torsion mechanism, a second link and a wiper arm drive system. The second end of the first link is hinged to the first end of the second link. The cleaning brush is hinged to the first end of the first link, and the rotation trajectory of the cleaning brush and the rotation trajectory of the hinge joint between the second end of the first link and the first end of the second link are both located in the first plane, or the rotation trajectory of the cleaning brush is located in a plane which is parallel to the first plane. The second link is driven to rotate by the wiper arm drive system, and the rotation trajectory of the second link and the rotation trajectory of the hinge joint are both located in the first plane, or the rotation trajectory of the second link is located in a plane which is parallel to the first plane. The torsion mechanism is configured to provide the first link and the second link with a force that rotates the first link relative to the second link.

In an embodiment, the torsion mechanism is configured to provide the first link and the second link with a force that rotates the first link and the second link away from each other.

In an embodiment, the torsion mechanism includes an energy storage element between the first link and the second link, and the energy storage element is configured to provide the first link and the second link with an elastic restoring force that rotates the first link and the second link away from each other.

In an embodiment, the energy storage element includes a torsion spring, a nitrogen gas spring and/or an elastic rubber band.

In an embodiment, the first link is an arc-shaped link.

In an embodiment, the wiper arm drive system includes a first watertight motor, and a second end of the second link is connected to an output end of the wiper arm drive system.

In an embodiment, the cleaning brush includes a cleaning blade, an arcuate sheet, a support sheet and a joint. The cleaning blade is installed on an inner concave surface of the arcuate sheet, and the arcuate sheet is connected to the support sheet. The joint is fixed on the support sheet, and the joint is hinged to the first end of the first link.

In an embodiment, the cleaning brush includes a protective cover, an inner side of the protective cover is installed on an outer convex surface of the arcuate sheet, and an outer side of the protective cover is configured as a gable roof.

In an embodiment, the cleaning brush includes a cleaning nozzle system provided on the support sheet.

In an embodiment, the cleaning brush includes an ultraviolet lamp system provided on the support sheet.

In an embodiment, the optical window cleaning device includes a base, a base power device and a guide rail. The wiper arm drive system is fixed on the base, the base power device is configured to drive the base to move along the guide rail, and a movement trajectory of the base power device is located in a second plane perpendicular to the first plane.

In an embodiment, the base includes a base support plate and a base motion mechanism. The wiper arm drive system is fixed on the base support plate, and the base support plate is matched with the guide rail through the base motion mechanism. The base motion mechanism has a degree of freedom (DOF) limiting structure that is nested and matched with the guide rail, and the DOF limiting structure is configured to restrict the base motion mechanism to move only along the guide rail.

In an embodiment, the base motion mechanism includes four base rollers. Two of the four base rollers are located on one side of the guide rail, another two of the four base rollers are located on the other side of the guide rail. The two base rollers located on the same side of the guide rail are staggered along the guide rail. The four base rollers are located on a same plane.

In an embodiment, the base power device includes a drive mechanism and a transmission mechanism, the drive mechanism is fixed to the base, and the drive mechanism cooperates with the guide rail through the transmission mechanism.

In an embodiment, the transmission mechanism includes a base power gear and a base rack, the base power gear is installed at an output end of the drive mechanism, the base rack is set along the guide rail, and the base power gear meshes with the base rack.

The present disclosure provides an underwater optical device, including: an optical window, and the optical window cleaning device as described above.

The present disclosure provides an optical window cleaning method, applying the optical window cleaning device as described above, and the optical window cleaning method includes: controlling the wiper arm drive system to drive the second link to rotate in the first plane or in a plane parallel to the first plane; and driving the first link and the cleaning brush to rotate in the first plane, or driving the first link and the cleaning brush to rotate in a plane parallel to the first plane. The torsion mechanism is configured to provide the first link and the second link with a force that rotates the first link relative to the second link, and the cleaning brush is closely attached to the optical window under a pressure of the first link.

In an embodiment, the optical window cleaning device includes a base, a base power device and a guide rail. The wiper arm drive system is fixed on the base, the base power device is configured to drive the base to move along the guide rail, and a movement trajectory of the base is located in a second plane perpendicular to the first plane. The optical window cleaning method includes: controlling the base power device to drive the base to move in the second plane along the guide rail.

It can be seen from the above technical solutions that the structure and action mode of the optical window cleaning device provided by the present disclosure can make the cleaning brush adapt to the optical windows of various curved shapes with varying curvatures, and keep the cleaning brush always in close contact with the optical window, so as to improve the cleaning effect.

The present disclosure also provides an optical window cleaning device and an underwater optical device. Since the optical window cleaning device and the underwater optical device apply the above-mentioned optical window cleaning device, the same beneficial effects can be obtained, and the foregoing description can be referred to.

BRIEF DESCRIPTION OF THE DRAWINGS

In order to more clearly illustrate the technical solutions in the embodiments of the present disclosure or in the prior art, the following briefly introduces the accompanying drawings that need to be used in the description of the embodiments or the prior art. Obviously, the drawings in the following description are only some embodiments of the present disclosure. For those of ordinary skill in the art, other drawings can also be obtained from these drawings without creative effort.

DETAILED DESCRIPTION OF THE EMBODIMENTS

The present disclosure provides a cleaning technique that can be used to prevent bio-fouling of an optical window surface on an underwater optical wireless communication device. The optical window of any curvature is cleaned by mechanical removal. It is possible to develop an optical window cleaning device, which consists of a cleaning brush, a wiper arm, a base, a base power device and a guide rail. When in use, the guide rail can be conveniently installed on various underwater devices equipped with underwater optical windows, and the cleaning brush runs along the guide rail to achieve the purpose of cleaning.

The technical solutions in the embodiments of the present disclosure will be clearly and completely described below with reference to the accompanying drawings in the embodiments of the present disclosure. Obviously, the described embodiments are only a part of the embodiments of the present disclosure, but not all of the embodiments. Based on the embodiments in the present disclosure, all other embodiments obtained by those of ordinary skill in the art without creative efforts shall fall within the protection scope of the present disclosure.

Figure 3:
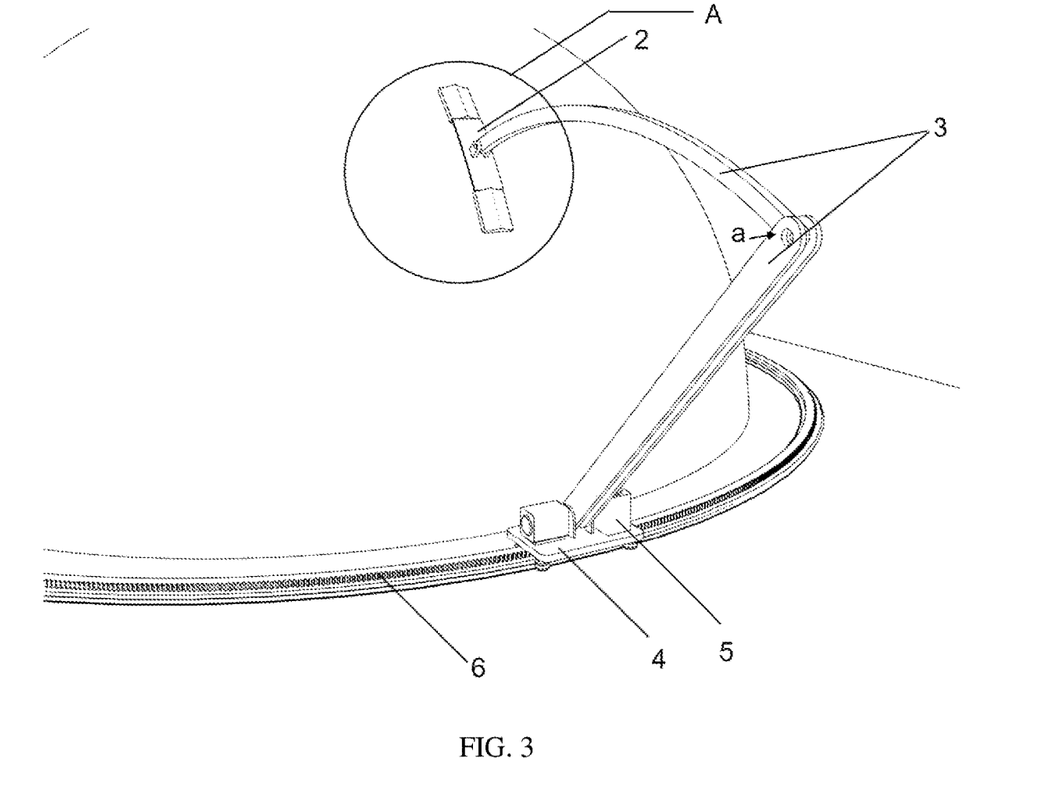
FIG. 3 is a schematic structural diagram of the optical window cleaning device according to an embodiment of the present disclosure.

The present disclosure provides an optical window cleaning device, including: a cleaning brush 2 and a wiper arm 3, and the structure can refer to FIG. 3.

Figure 6:
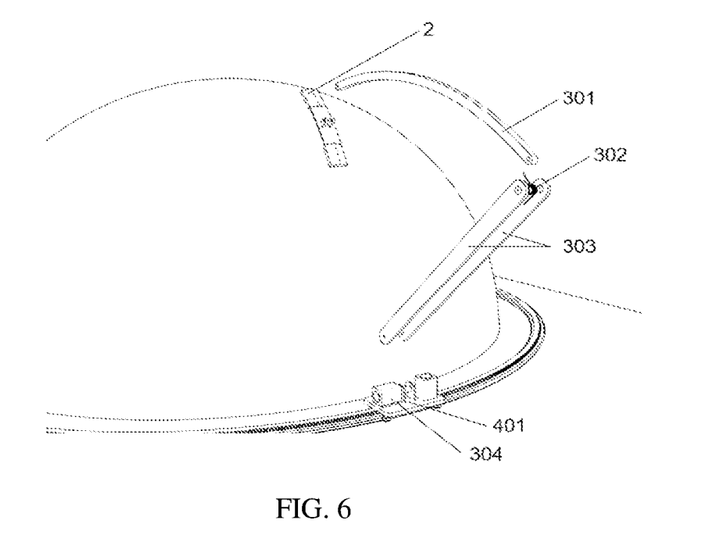
FIG. 6 is a schematic structural diagram of a wiper arm of the optical window cleaning device according to an embodiment of the present disclosure.

The wiper arm 3 includes a first link 301, a torsion mechanism 302, a second link 303 and a wiper arm drive system 304, and the structure can refer to FIG. 6.

A second end of the first link 301 is hinged to a first end of the second link 303.

The cleaning brush 2 is hinged to a first end of the first link 301, and a rotation trajectory of the cleaning brush 2 and a rotation trajectory of a hinge joint a between the second end of the first link 301 and the first end of the second link 303 are both located in a first plane, or the rotation trajectory of the cleaning brush 2 is located in a plane which is parallel to the first plane.

The second link 303 is driven to rotate by the wiper arm drive system 304, and a rotation trajectory of the second link 303 and the rotation trajectory of the hinge joint a are both located in the first plane, or the rotation trajectory of the second link 303 is located in the plane which is parallel to the first plane.

Figure 9A:
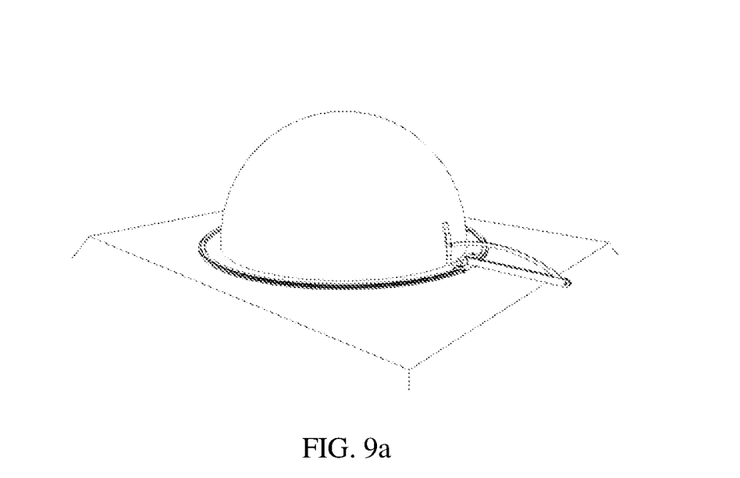
FIG. 9a, FIG. 9b and FIG. 9c are working state diagrams of the optical window cleaning device of the present disclosure along a warp direction of a variable curvature surface.
Figure 9B:
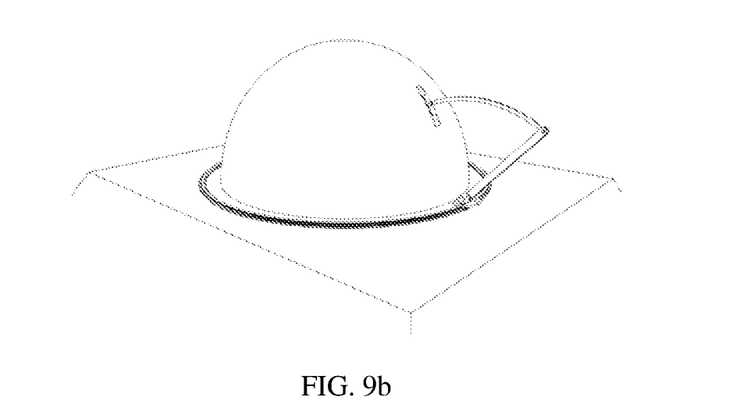
Figure 9C:
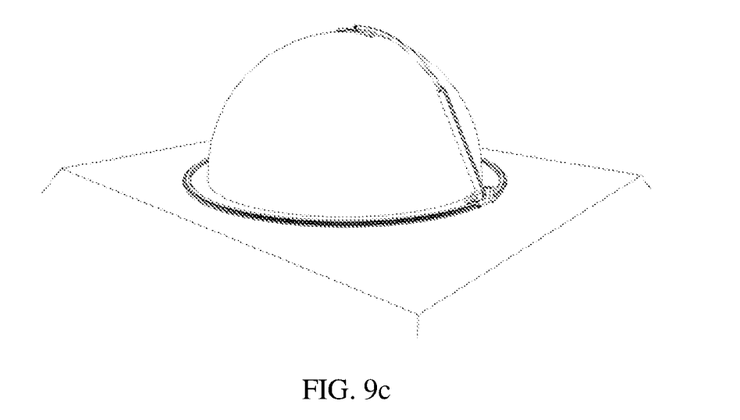

The torsion mechanism 302 can provide the first link 301 and the second link 303 with a force that rotates the first link 301 relative to the second link 303, so that the cleaning brush 2 can be in close contact with the optical window 1 of the optical window surface, and the structure can refer to FIG. 9a, FIG. 9b and FIG. 9c.

During operation, the wiper arm drive system 304 is fixed to the base 4.

The wiper arm drive system 304 controls the rotation of the second link 303, and drives the first link 301 to rotate through the hinge joint a. Under the support of the torsion mechanism 302 and the wiper arm drive system 304, the cleaning brush 2 is subjected to the pressure exerted by the first link 301 and the supporting force of the optical window 1, so that the cleaning brush 2 is tightly attached to the optical window 1. Controlling the wiper arm drive system 304 to rotate the second link 303 to different positions will drive the cleaning brush 2 to move in the first plane (the cleaning brush 2 moves along the warp direction of the spherical optical window 1. For the convenience of description, the first plane is described along the warp direction. The protection scope of this solution is not limited to this. The first plane can also be other structures that do not pass through the center of the sphere, or the optical window 1 is non-spherical), and the cleaning brush 2 is always tightly attached to the optical window 1.

It can be seen from the above technical solutions that the structure and action mode of the optical window cleaning device provided by the present disclosure can make the cleaning brush 2 adapt to the optical windows 1 of various curved shapes with varying curvatures, and keep the cleaning brush 2 always in close contact with the optical window 1, so as to improve the cleaning effect.

In an embodiment, the torsion mechanism 302 can provide the first link 301 and the second link 303 with a force that rotates the first link 301 and the second link 303 away from each other, and is especially suitable for the hemispherical optical window 1 in this embodiment. Of course, the torsion mechanism 302 can also be designed to provide the first link 301 and the second link 303 with a force that rotates the first link 301 and the second link 303 towards each other (i.e., approaching), so as to make the cleaning brush 2 tightly attach to the optical window 1.

The torsion mechanism 302 includes an energy storage element between the first link 301 and the second link 303.

The energy storage element can provide the first link 301 and the second link 303 with a force that rotates the first link 301 and the second link 303 away from each other. The torsion mechanism 302 adopts an energy storage element, and can automatically control the flexure between the first link 301 and the second link 303 under the elastic restoring force, and has a simple structure. Linear push rods or other structures can also be added to control the compression and expansion between the rods, and the actions are controlled by means of sensors, which will not be repeated here.

In order to further optimize the above technical solution, the energy storage element includes a torsion spring, which can provide a reliable elastic restoring force. Through the selection, the torsion spring can be kept in a compressed state all the time, so as to provide the first link 301 and the second link 303 with a force that rotates the first link 301 and the second link 303 away from each other. The torsion spring can also be changed to other energy storage elements, such as nitrogen gas springs, high elastic rubber bands, or the like.

In an embodiment, the first link 301 is an arc-shaped link, which can better adapt to the curvature change of the optical window 1, avoid interference with the optical window 1 during movement, and keep the cleaning brush 2 pressed tightly, thereby expanding the cleaning range. The arc-shaped first link 301 is especially suitable for the spherical optical window 1 in this embodiment. Further, the curvature of the first link 301 is matched with the optical window 1, the effect of avoiding interference is better, and the cleaning range is larger. The first link 301 is not limited to an arc shape, and may also have other structures, and is shaped to fit the curvature change of the optical window 1.

In this embodiment, the wiper arm drive system 304 includes a first watertight motor.

A second end of the second link 303 is connected to an output end of the wiper arm drive system 304. The wiper arm drive system 304 uses the first watertight motor to drive the second link 303 to rotate, has a simple structure and is suitable for underwater environments. The wiper arm drive system 304 can also be equipped with mechanisms such as reducers in combination with specific usage scenarios, such as motor+reducer or motor+other actuators, which will not be repeated here.

Figure 4:
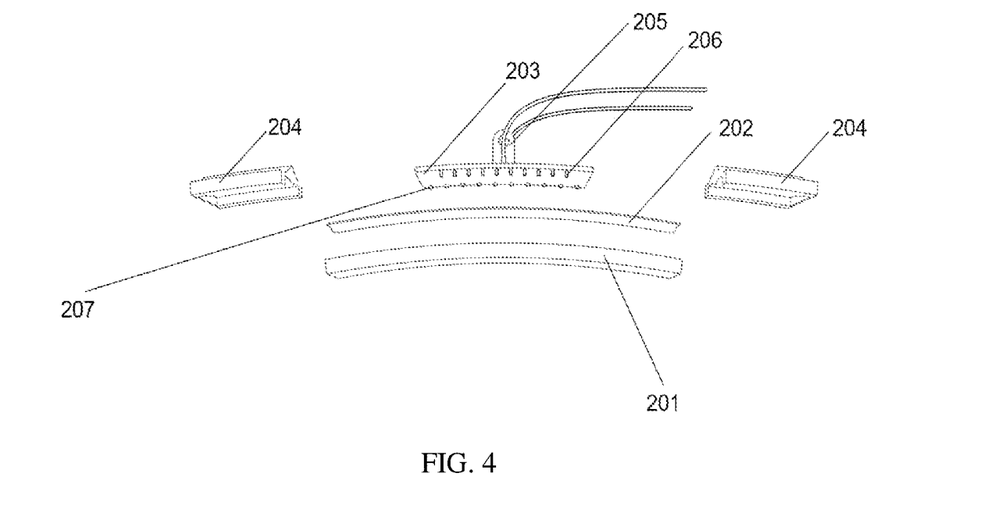
FIG. 4 is an enlarged view of the optical window cleaning device at portion A according to an embodiment of the present disclosure, that is, a schematic structural diagram of a cleaning brush of an embodiment of the present disclosure.

In an embodiment, the cleaning brush 2 includes a cleaning blade 201, an arcuate sheet 202, a support sheet 203 and a joint 205, the structure can refer to FIG. 4.

The cleaning blade 201 is installed on an inner concave surface of the arcuate sheet 202, the arcuate sheet 202 is connected to the support sheet 203, the joint 205 is fixed on the support sheet 203, and the joint 205 is hinged to the first end of the first link 301. The arcuate sheet 202 has certain toughness and strength, and under the pressure exerted by the first link 301 and the action of the optical window 1, the cleaning blade 201 will be in close contact with the optical window 1. The above is a division of the structure of the cleaning brush 2 from a functional point of view. A plurality of components can also be designed as an integrated structure, such as the arcuate sheet 202 and the support sheet 203, the support sheet 203 and the joint 205, or the like, to improve the integration degree.

Further, the cleaning brush 2 further includes a protective cover 204.

The inner side of the protective cover 204 is installed on the outer convex surface of the arcuate sheet 202 to protect and beautify the appearance. The outer side of the protective cover 204 is designed as a gable roof, and the water pressure is formed when the cleaning brush 2 moves, so that the cleaning blade 201 can be better in close contact with the optical window 1.

In an embodiment, the cleaning brush 2 further includes a cleaning nozzle system 206 provided on the support sheet 203. Through the infusion tube 2083 connected to the washing mechanism, the cleaning nozzle system 206 continuously sprays disinfectant during the operation of the cleaning brush to clean the optical window 1 and the cleaning blade 201, kill the attached marine organisms, which can ensure the long-term use of the cleaning brush 2 without reducing the cleaning effect. The structure of the washing mechanism can refer to FIG. 5.

In an embodiment, the cleaning brush 2 further includes an ultraviolet lamp system 207 provided on the support sheet 203. The ultraviolet lamp system 207 continuously emits ultraviolet rays to illuminate the optical window 1 and the cleaning blade 201 during the working process of the cleaning brush 2 to further kill the attached marine organisms, which can ensure the long-term use of the cleaning brush 2 without reducing the cleaning effect.

The optical window cleaning device provided by the embodiments of the present disclosure further includes a base 4, a base power device 5 and a guide rail 6, and the structure can refer to FIG. 3.

The wiper arm drive system 304 is fixed on the base 4, the base power device 5 can drive the base 4 to move along the guide rail 6, and a movement trajectory of the base power device 5 is located in a second plane perpendicular to the first plane, to cover a larger range of the optical window 1 and improve the cleaning effect.

The situation shown in FIG. 3 is taken as an example, when the cleaning brush 2 is at a certain height from the plane of the guide rail 6, due to the support and limit of the guide rail 6, the base 4 will resist the force exerted on the base 4 by the structure of the wiper arm 3 on it and the external environment (such as underwater ocean current). The wiper arm drive system 304 controls the rotation of the second link 303, and drives the first link 301 to rotate through the hinge joint a. Under the support of the torsion mechanism 302 (such as the tension force compressed by the torsion spring), the wiper arm drive system 304, the base 4 and the guide rail 6, the cleaning brush 2 is subjected to the pressure exerted by the first link 301 and the supporting force of the optical window 1, so that the cleaning brush 2 is in close contact with the optical window 1. The base power device 5 drives the base 4 to move along the guide rail 6, and can also control the wiper arm drive system 304 to rotate the second link 303 to different positions, the cleaning brush 2 will be driven to move in the second plane (here, the cleaning brush 2 moves along the weft direction of the optical window 1), and will always be in close contact with the surface. This structure and action mode can make the cleaning brush 2 adapt to various curved shapes with varying curvatures along the weft direction of the curved surface of the optical window 1, and keep the cleaning brush 2 in a state of close contact with the optical window 1 all the time.

In an embodiment, the base 4 includes a base support plate 401 and a base motion mechanism.

The wiper arm drive system 304 is fixed on the base support plate 401, and the base support plate 401 is matched with the guide rail 6 through the base motion mechanism, the base motion mechanism has a degree of freedom (DOF) limiting structure that is nested and matched with the guide rail 6, and the DOF limiting structure restricts the base motion mechanism to move only along the guide rail 6, such that the base 4 can adapt to complex ocean currents and move smoothly along the guide rails 6.

Further, the base motion mechanism includes four base rollers 402.

Two of the four base rollers 402 are located on one side of the guide rail 6, another two of the four base rollers 402 are located on the other side of the guide rail 6, the two base rollers 402 located on a same side of the guide rail 6 are staggered along the guide rail 6; the four base rollers 402 are located on a same plane. The four base rollers 402 form the DOF limiting structure, and the structure can refer to FIG.

Figure 7A:
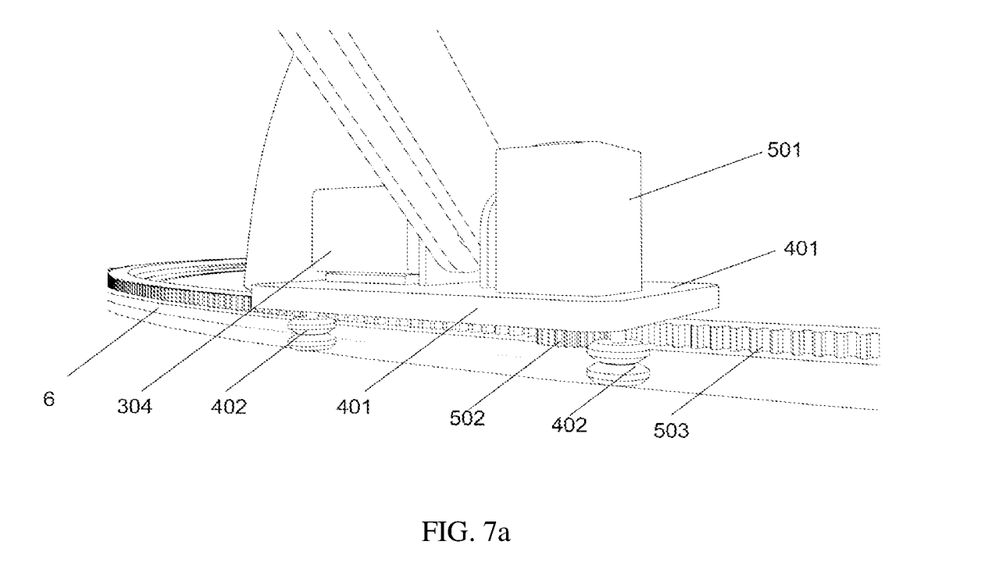
FIG. 7a, FIG. 7b and FIG. 7c are schematic structural diagrams of a base and a guide rail of the optical window cleaning device according to an embodiment of the present disclosure.
Figure 7B:
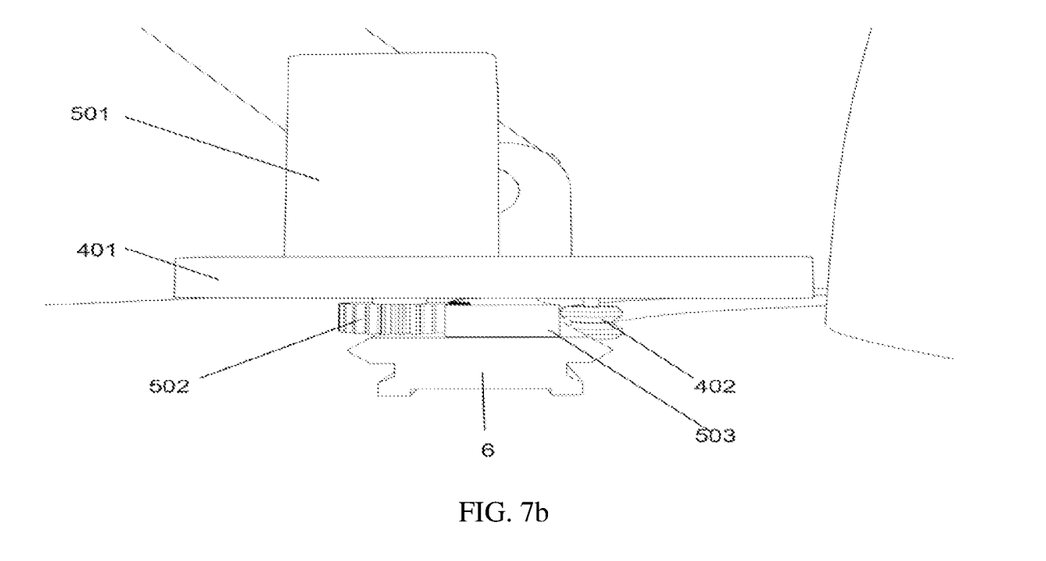
Figure 7C:
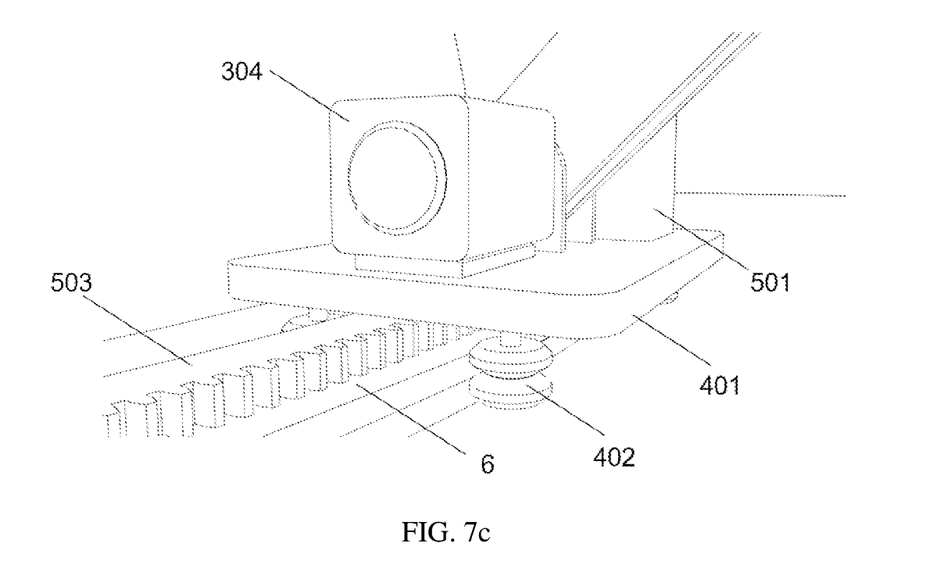
Figure 8:
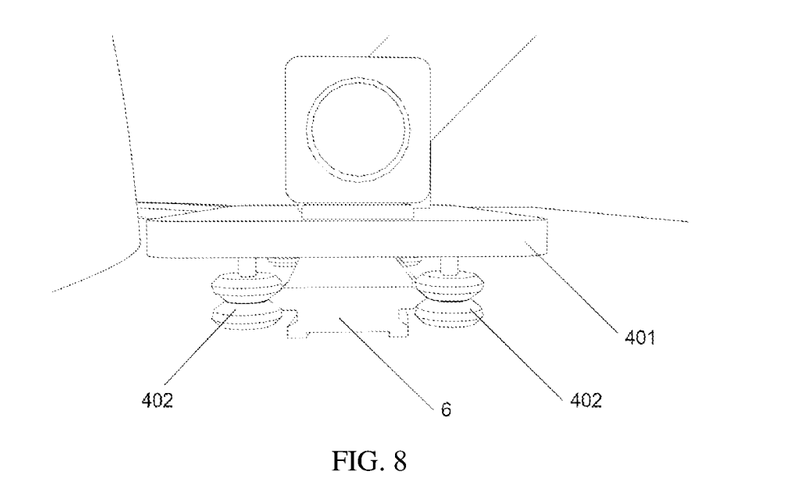
FIG. 8 is a cross-sectional view showing cooperation between a base roller and the guide rail of the optical window cleaning device according to an embodiment of the present disclosure.

7a, FIG. 7b, FIG. 7c and FIG. 8 to limit the DOF of the base 4 in all directions, and only retain the DOF along the movement direction of the guide rail 6. When the base 4 runs relative to the guide rail 6, the four base rollers 402 rotate along its own axis in the convex groove of the guide rail 6, the friction force between the base 4 and the guide rail 6 is greatly reduced, so that the base 4 can adapt to the complex ocean currents at the bottom of the water and move smoothly along the guide rail 6. The matching mode between the base 4 and the guide rail 6 can be realized by using an alternative structure, for example, the number of the base rollers 402 is not limited to four, as long as the cleaning brush 2 and the wiper arm 3 can move smoothly along the guide rail 6 and resist the force of the ocean current and the optical window 1.

In this embodiment, the base power device 5 includes a drive mechanism and a transmission mechanism.

The drive mechanism is provided on the base 4, and the drive mechanism can cooperate with the guide rail 6 through the transmission mechanism. In an embodiment, the drive mechanism includes a second watertight motor 501, which has a simple structure and is suitable for underwater environments, and can also be equipped with mechanisms such as a reducer in combination with specific usage scenarios, such as motor+reducer or motor+other actuators.

In an embodiment, the transmission mechanism 5 includes a base power gear 502 and a base rack 503.

The base power gear 502 is provided at an output end of the drive mechanism, the base rack 503 is provided along the guide rail 6, and the base power gear 502 meshes with the base rack 503. The base 4 is driven by the drive mechanism, so that the base power gear 502 meshes with the fixed base rack 503 installed on the guide rail 6, and drives the wiper arm 3 and the cleaning brush 2 to run along the direction of the guide rail 6. Other transmission modes such as belt transmission, chain transmission, or the like, can also be used, as long as the cleaning brush 2 and the wiper arm 3 can move along the guide rail 6.

The solution is further introduced below in conjunction with specific embodiments.

Figure 2A:
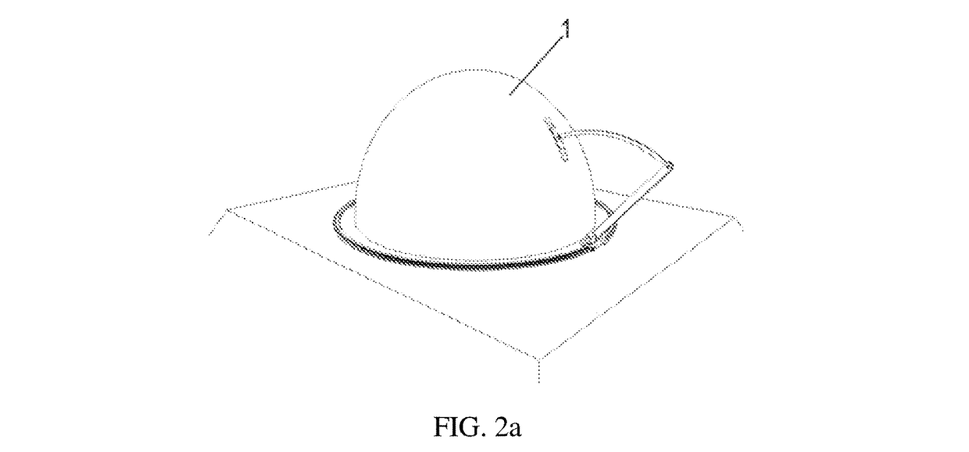
FIG. 2a, FIG. 2b and FIG. 2c are application scenario diagrams of an optical window cleaning device of the present disclosure.
Figure 2B:
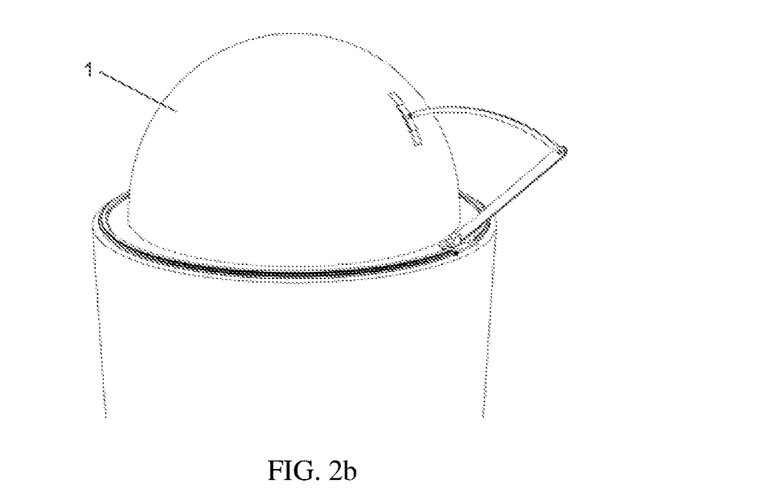
Figure 2C:
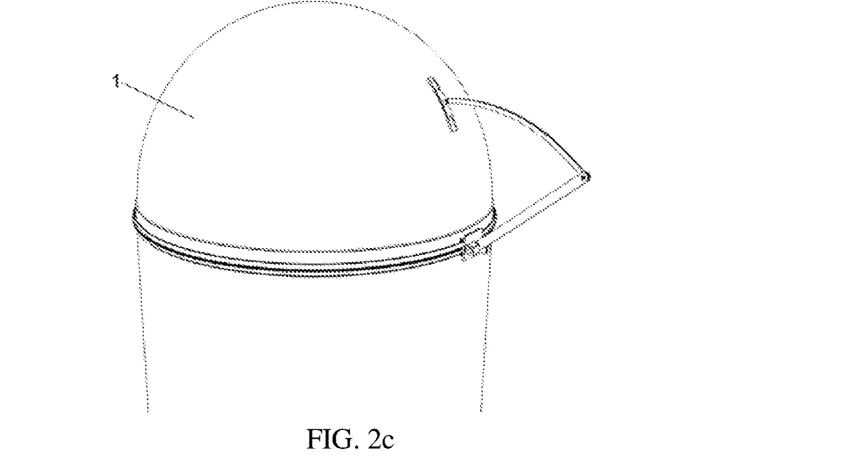

FIG. 2a, FIG. 2b and FIG. 2c are diagrams of application scenarios of a device of the present disclosure. 1 is an optical window with changing curvature (here, an optical curved lens is taken as an example), which can be placed on a seabed base or mounted on any other underwater device. FIG. 3 is a schematic structural diagram of an optical window cleaning device of the present disclosure (here, an underwater lens cleaning device is taken as an example), and the device includes a cleaning brush 2, a wiper arm 3, a base 4, a base power device 5 and a guide rail 6.

FIG. 4 is a structural diagram of the cleaning brush 2 of the device, which includes a cleaning blade 201, an arcuate sheet 202, a support sheet 203, a protective cover 204, a joint 205, a cleaning nozzle system 206 and an ultraviolet lamp system 207. The cleaning blade 201 is made of rubber, and the function is to wipe off the attached organisms and impurities on the glass of the optical window 1. The arcuate sheet 202 is connected to the cleaning blade 201 and the support sheet 203, and has certain toughness and strength. The arcuate sheet 202 can be specifically anti-rust steel sheet, which is bow-shaped when leaving the factory. Under the action of the pressure exerted by the first link 301 and the support force of the surface, the cleaning blade 201 will be in close contact with the optical window surface. The support sheet 203 is connected to the protective cover 204, the arcuate sheet 202 and the joint 205, and is made of a metal anti-rust material with good rigidity and strength, or other materials with comparable strength. The joint 205 is used to connect the support sheet 203 and the wiper arm 3. The protective cover 204 is used for wrapping and protecting the cleaning blade 201, the arcuate sheet 202 and other structures to protect and beautify the appearance, and can be a rubber cover. The shape of the upper part of the protective cover 204 is designed as a gable roof, and the water pressure is formed when the cleaning device moves, so that the cleaning blade 201 can be better in close contact with the optical glass surface. A cleaning nozzle system 206 is installed on one side of the support sheet 203, and by connecting the nozzle joint to the infusion tube 2803, the cleaning nozzle system 206 continuously sprays the disinfectant during the working process of the cleaning brush 2 to clean the glass and the cleaning blade 201 and kill the attached sea creatures. An ultraviolet lamp system 207 is installed on the other side of the support sheet 203. During the operation of the cleaning brush 2, the ultraviolet lamp system 207 continuously emits ultraviolet rays to irradiate the glass surface and the cleaning blade 201 to further kill the attached marine organisms. Due to the action of the disinfectant and the irradiation of the ultraviolet lamp, the organisms attached to the cleaning brush 2 are eliminated, which can ensure the long-term use of the cleaning device without reducing the cleaning effect.

Figure 5:
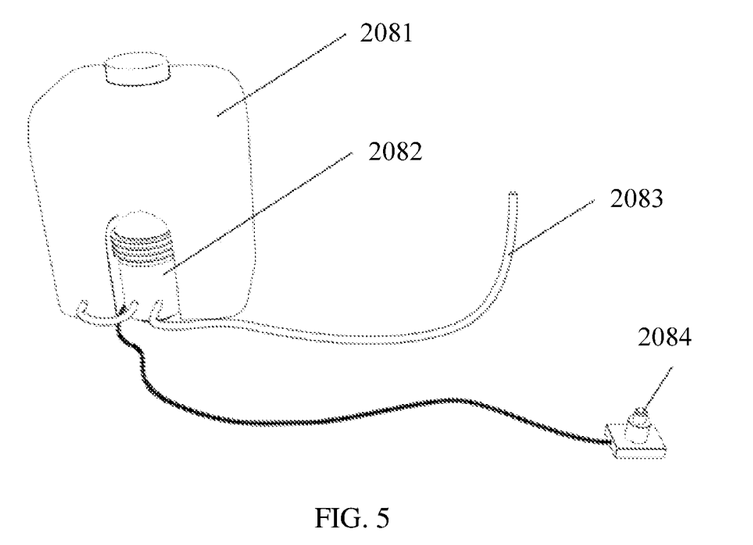
FIG. 5 is a schematic structural diagram of a washing mechanism of the optical window cleaning device according to an embodiment of the present disclosure.

FIG. 5 is a schematic diagram of the washing mechanism of the seabed cleaning device of the present disclosure. As shown in FIG. 5, the washing device includes a liquid storage tank 2801, a washing pump 2802, an infusion pipe 2803 and a spray switch 2804 and the like. The device is placed in an underwater device equipped with an optical window. When the seabed cleaning device is working, the spray switch 2084 starts, the washing pump 2082 compresses the disinfectant in the liquid storage tank 2081 and delivers the disinfectant to the cleaning nozzle system 206 of the cleaning brush through the infusion pipe 2083, so as to wash and destroy the attached marine organisms during the operation of the cleaning brush 2.

FIG. 6 is a schematic structural diagram of the wiper arm 3 of the seabed lens cleaning device of the present disclosure. As shown in FIG. 6, the wiper arm 3 includes a first link 301, a torsion mechanism 302, a second link 303 and a wiper arm drive system 304. One end of the first link 301 is hinged with the joint 205, and the other end of the first link 301 is hinged with the second link 303, and has a certain strength. The first link 301 is an arc-shaped link to avoid interference with the optical window surface, and further expand the cleaning range. One end of the second link 303 is hinged with the first link 301, and the other end of the second link 303 is connected to the output end of the wiper arm drive system 304 and the connection port on the base support plate 401. The first link 301 and the second link 303 are provided with the torsion mechanism 302 inside the hinge joints. The wiper arm drive system 304 is a first watertight motor (which can be equipped with a mechanism such as a reducer in combination with specific usage scenarios), and the output end of the wiper arm drive system 304 is connected to the second link 303, the rotational speed and torque of the drive system are transmitted to the second link 303, and the wiper arm drive system 304 is fixed on the base support plate 401.

FIG. 7a, FIG. 7b and FIG. 7c are schematic diagrams of the base and the guide rail 6 of the seabed lens cleaning device of the present disclosure. FIG. 8 is a cross-sectional view showing cooperation between the base roller and the guide rail 6 of the seabed lens cleaning device of the present disclosure. The base 4 includes a base support plate 401 and four base rollers 402. A wiper arm structure and a cleaning brush are mounted on the base support plate 401. The four base rollers 402 cooperate with the guide rail 6. It can be seen from FIG. 8 that the guide rail 6 is nested and matched with the four base rollers 402 to limit the DOF of the base 4 in all directions, and only retain the DOF along the movement direction of the guide rail. When the base 4 runs relative to the guide rail, the four rollers rotate along their own axis in the convex groove of the guide rail, which greatly reduces the friction force between the base 4 and the guide rail 6 during the movement process, so that the device can adapt to the complex ocean currents on the bottom of the water and move smoothly along the guide rail. The base power device 5 includes a second watertight motor 501 (which can be equipped with mechanisms such as a reducer in combination with a specific usage scenario), a base power gear 502 and a base rack 503. The second watertight motor 501 is fixed on the base support plate 401. The base power gear 502 is fixed on the output shaft of the second watertight motor 501 and meshes with the base rack. When working, the watertight motor 501 is activated, and the motor transmits the rotational speed and torque to the base power gear 502 and drives the device to move along the circular guide rail through meshing with the base rack.

When working, the base power device 5 is activated, the seabed lens cleaning device will reciprocate circumferentially along the circular arc guide rail 6. When the seabed lens cleaning device is at a certain position on the circumference of the guide rail 6, the base 4 will resist the force exerted by the wiper arm structure and the underwater ocean current due to the support and limit of the guide rail 6. The wiper arm drive system 304 controls the second link 303 to rotate along the hinge joint a, and the torsion mechanism 302 is always in a compressed state. Under the support of the tension of the torsion mechanism 302, the motor torque of the wiper arm drive system and the guide rail of the base, the cleaning brush is subjected to the pressure exerted by the first link 301 and the support force of the optical window surface, so that it is tightly attached to the surface. By controlling the wiper arm drive system 304 to rotate the second link 303 to different positions, the cleaning brush will be driven to move along the warp direction of the optical glass surface, and will always be in close contact with the surface. This structure and action mode can make the cleaning brush adapt to various curved surface shapes with changing curvature along the warp direction of the curved surface of the glass, and keep the cleaning brush always in close contact with the optical surface of the optical glass. FIG. 9a, FIG. 9b and FIG. 9c are the working state diagrams of the cleaning brush and the wiper arm mechanism along the warp direction of the surface when the seabed lens cleaning device is at a certain circumferential position of the circular track.

When the seabed lens cleaning device is at a certain height from the plane of the guide rail 6, the base 4 will resist the force exerted by the wiper arm structure and the underwater ocean current due to the support and limit of the guide rail 6. The wiper arm drive system 304 controls the second link 303 to rotate along the hinge joint a, and the torsion mechanism 302 is always in a compressed state. Under the support of the tension of the torsion mechanism 302, the motor torque of the wiper arm drive system and the guide rail of the base, the cleaning brush is subjected to the pressure exerted by the first link 301 and the support force of the surface, so that it is tightly attached to the glass surface. The base power device 5 is driven to drive the base power gear 502 to mesh with the base rack 503, the drive device moves along the circumferential direction of the guide rail, and controlling the wiper arm drive system 304 to rotate the second link 303 to different positions will drive the cleaning brush to always stick to the surface along the weft direction of the optical glass surface. This structure and action mode can make the cleaning brush adapt to various curved shapes with changing curvature along the weft direction of the curved surface of the glass, and keep the cleaning brush always in close contact with the surface of the optical glass.

Compared with the prior art, the advantages of this solution are as follows:

1. Wide range of applications, suitable for cleaning surfaces of polyhedral windows and spherical windows with varying curvatures (different shapes of guide rails 6 need to be equipped in combination with specific usage scenarios).

2. The structure of the underwater device equipped with the optical surface does not change, suitable for various underwater devices.

3. Combined with the usage scenario of the underwater cleaning device and the force of the cleaning brush, except for spraying disinfectant and ultraviolet light system, the cleaning action of the whole device is only completed by one wiper arm drive motor and base drive motor. The structure is simple and compact, no complicated mechanism is introduced, the parts and drive devices are few, the cost is low, the effect is good, and the maintenance is easy.

4. The cleaning device is used in conjunction with the guide rail 6 to be used in the seabed environment. The mechanism is simple and exquisite, which can adapt to complex underwater currents and ensure the reliability of the mechanism.

5. Because the mechanism continuously sprays disinfectant and irradiates ultraviolet rays during the working process, it can not only strengthen the effect of eliminating attachments, but also self-clean the cleaning brush, so that the mechanism can maintain a good cleaning effect for a long time.

The embodiment of the present disclosure further provides an underwater device, including: an optical window 1, and the above-mentioned optical window cleaning device. The underwater device can meet the cleaning needs of the optical surface whose curvature changes along the warp and weft directions. The structure is simple and exquisite, the scope of application is wide, the parts and drive devices are few, the cost is low, the effect is good, and the maintenance is easy.

The embodiment of the present disclosure also provides an optical window cleaning method, applying the above optical window cleaning device, and the optical window cleaning method includes: controlling the wiper arm drive system 304 to drive the second link 303 to rotate in the first plane or in a plane parallel to the first plane; and driving the first link 301 and the cleaning brush 2 to rotate in the first plane, or driving the first link 301 and the cleaning brush 2 to rotate in a plane parallel to the first plane. The torsion mechanism 302 provides the first link 301 and the second link 303 with a force that rotates the first link 301 relative to the second link 303, and the cleaning brush 2 is closely attached to the optical window 1 under a pressure of the first link 301. The cleaning brush 2 moves along the warp direction of the spherical optical window 1, and the detailed working process can be referred to the previous description, which will not be repeated here.

Further, the optical window cleaning method includes: controlling the base power device 5 to drive the base 4 to move in the second plane along the guide rail 6. The base 4 moves along the weft direction of the spherical optical window 1, and the detailed working process can be referred to the previous description, which will not be repeated here. The movements of the first and second planes described above can be performed simultaneously.

To sum up, the present disclosure provides a cleaning technique that can be used to prevent bio-fouling of an optical window surface on an underwater optical wireless communication device. The feature of the present disclosure is that the optical window of any curvature is cleaned by means of mechanical removal. It is possible to develop an optical window cleaning device, which includes a cleaning brush, a wiper arm, a base, a base power device and a guide rail. When in use, the guide rail can be conveniently installed on various underwater devices equipped with underwater optical windows, and the cleaning brush runs along the guide rail to achieve the purpose of cleaning. The core advantage of the device lies in the simple mechanism and the seabed optical window that can adapt to various curvatures.

The various embodiments in this specification are described in a progressive manner, and each embodiment focuses on the differences from other embodiments, and the same and similar parts between the various embodiments can be referred to each other.

The above description of the disclosed embodiments enables any person skilled in the art to implement or use the present disclosure. Various modifications to these embodiments will be readily apparent to those skilled in the art, and the generic principles defined herein may be implemented in other embodiments without departing from the spirit or scope of the present disclosure. Therefore, the present disclosure is not intended to be limited to the embodiments shown herein, but is to be accorded with the widest scope consistent with the principles and novel features disclosed herein.

What is claimed is:

1. An optical window cleaning device, comprising:
   a cleaning brush; and
   a wiper arm;
   wherein:
   the wiper arm comprises a first link, a torsion mechanism, a second link and a wiper arm drive system;
   a second end of the first link is hinged to a first end of the second link;
   the cleaning brush is hinged to a first end of the first link, and a rotation trajectory of the cleaning brush and a rotation trajectory of a hinge joint between the second end of the first link and the first end of the second link are both located in a first plane, or the rotation trajectory of the cleaning brush is located in a plane which is parallel to the first plane;
   the second link is driven to rotate by the wiper arm drive system, and a rotation trajectory of the second link and the rotation trajectory of the hinge joint are both located in the first plane, or the rotation trajectory of the second link is located in the plane which is parallel to the first plane;
   the torsion mechanism is configured to provide the first link and the second link with a force that rotates the first link relative to the second link;
   the cleaning brush comprises a cleaning blade, an arcuate sheet, a support sheet and a joint;
   the cleaning blade is installed on an inner concave surface of the arcuate sheet, and the arcuate sheet is connected to the support sheet;
   the joint is fixed on the support sheet, and the joint is hinged to the first end of the first link; and
   the cleaning brush further comprises an ultraviolet lamp system provided on the support sheet.

2. The optical window cleaning device of claim 1, wherein the torsion mechanism is configured to provide the first link and the second link with a force that rotates the first link and the second link away from each other.

3. The optical window cleaning device of claim 1, wherein the torsion mechanism comprises an energy storage element between the first link and the second link, and the energy storage element is configured to provide the first link and the second link with an elastic restoring force that rotates the first link and the second link away from each other.

4. The optical window cleaning device of claim 3, wherein the energy storage element comprises a torsion spring, a nitrogen gas spring and/or an elastic rubber band.

5. The optical window cleaning device of claim 1, wherein the first link is an arc-shaped link.

6. The optical window cleaning device of claim 1, wherein the wiper arm drive system comprises a first water-tight motor, and a second end of the second link is connected to an output end of the wiper arm drive system.

7. The optical window cleaning device of claim 1, wherein the cleaning brush further comprises a protective cover, an inner side of the protective cover is installed on an outer convex surface of the arcuate sheet, and an outer side of the protective cover is configured as a gable roof.

8. The optical window cleaning device of claim 1, wherein the cleaning brush further comprises a cleaning nozzle system provided on the support sheet.

9. The optical window cleaning device of claim 1, further comprising: a base, a base power device and a guide rail;
   wherein the wiper arm drive system is fixed on the base, the base power device is configured to drive the base to move along the guide rail, and a movement trajectory of the base power device is located in a second plane perpendicular to the first plane.

10. The optical window cleaning device of claim 9, wherein the base comprises a base support plate and a base motion mechanism;
    the wiper arm drive system is fixed on the base support plate, and the base support plate is matched with the guide rail through the base motion mechanism; and
    the base motion mechanism has a degree of freedom (DOF) limiting structure that is nested and matched with the guide rail, and the DOF limiting structure is configured to restrict the base motion mechanism to move only along the guide rail.

11. The optical window cleaning device of claim 10, wherein the base motion mechanism comprises four base rollers;
    two of the four base rollers are located on one side of the guide rail, another two of the four base rollers are located on the other side of the guide rail;
    the two base rollers located on a same side of the guide rail are staggered along the guide rail; and
    the four base rollers are located on a same plane.

12. The optical window cleaning device of claim 9, wherein the base power device comprises a drive mechanism and a transmission mechanism, the drive mechanism is fixed to the base, and the drive mechanism cooperates with the guide rail through the transmission mechanism.

13. The optical window cleaning device of claim 12, wherein the transmission mechanism comprises a base power gear and a base rack, the base power gear is installed at an output end of the drive mechanism, the base rack is set along the guide rail, and the base power gear meshes with the base rack.

14. An underwater optical device, comprising: an optical window, and the optical window cleaning device of claim 1.

15. An optical window cleaning method, applying the optical window cleaning device of claim 1, wherein the optical window cleaning method comprises:
controlling the wiper arm drive system to drive the second link to rotate in the first plane or in a plane parallel to the first plane; and
driving the first link and the cleaning brush to rotate in the first plane, or driving the first link and the cleaning brush to rotate in a plane parallel to the first plane;
wherein the torsion mechanism is configured to provide the first link and the second link with a force that rotates the first link relative to the second link, and the cleaning brush is attached to the optical window to achieve cleaning under a pressure of the first link.

16. The optical window cleaning method of claim 15, wherein the optical window cleaning device further comprises a base, a base power device and a guide rail;
wherein the wiper arm drive system is fixed on the base, the base power device is configured to drive the base to move along the guide rail, and a movement trajectory of the base power device is located in a second plane perpendicular to the first plane;
the optical window cleaning method further comprises:
controlling the base power device to drive the base to move in the second plane along the guide rail.

\* \* \* \* \*